United States Patent [19]

Selsted et al.

[11] Patent Number: 5,324,716
[45] Date of Patent: Jun. 28, 1994

[54] BROAD SPECTRUM ANTIMICROBIAL COMPOUNDS AND METHODS OF USE

[75] Inventors: Michael E. Selsted, Irvine; James S. Cullor, Woodland, both of Calif.

[73] Assignee: Regents of the University of California, Oakland, Calif.

[21] Appl. No.: 715,271

[22] Filed: Jun. 14, 1991

[51] Int. Cl.$^5$ .................... A61K 37/00; A61K 37/02; C07K 5/00; C07K 7/00
[52] U.S. Cl. ........................ 514/14; 514/12; 530/324; 530/327
[58] Field of Search .................. 514/12, 14; 530/324, 530/327

[56] References Cited

U.S. PATENT DOCUMENTS 4,543,252 9/1985 Lehrer et al. .................. 514/12

OTHER PUBLICATIONS

Diamond et al., "Tracheal antimicrobial peptide, a cysteine-rich peptide from mammalian tracheal mucosa: Peptide isolation and cloning of a cDNA" Proc. Natl. Acad. Sci. USA 88:3952–3956 (1991).
Boman, Hans G., "Antibacterial Peptides: Key Components Needed in Immunity" Cell 65:205–207 (1991).
Zanetti et al., "Bactenecins, Defense Polypeptides of Bovine Neutrophils, Are Generated from Precursor Molecules Stored in the Large Granules" The Journal of Cell Biology 111:1363–1371 (1990).
Selsted et al., "Purification and Antibacterial Activity of Antimicrobial Peptides of Rabbit Granulocytes" Infection and Immunity 45:150–154 (1984).
Frank et al., J. of Biol Chem., vol. 265, No. 31, pp. 18871–18874, 1990.
Nagalakskmi et al., Chem. Abstrs., vol. 101, p. 492, Ab No. 22133b, 1984.
Fox et al., Chem. Abstrs., vol. 107, p. 529, Abst No. 233726j, 1987.
Shimokawa et al., Chem. Abstrs, vol. 114, p. 406, Abst No. 235045e, 1991.

Primary Examiner—Lester L. Lee
Assistant Examiner—A. M. Davenport
Attorney, Agent, or Firm—Campbell and Flores

[57] ABSTRACT

The invention provides a broad spectrum antimicrobial compound that includes a tryptophan-rich peptide exhibiting antimicrobial activity. A method of microbicidal inhibition or microbistatic inhibition of microbial growth is also provided. The method includes administering to an environment capable of sustaining microbial growth a microbicidally or microbistatically effective amount of a tryptophan-rich peptide exhibiting antimicrobial activity.

15 Claims, 4 Drawing Sheets 1 2 3 4

BROAD SPECTRUM ANTIMICROBIAL COMPOUNDS AND METHODS OF USE

This invention was made with Government support under Grant No. AI-22931 awarded by the National Institutes of Health. The Government has certain rights in this invention.

BACKGROUND

This invention relates generally to microbicidal compounds and, more particularly, to broad spectrum tryptophan-rich peptide known as indolicidin.

Infectious diseases are a primary cause of morbidity and mortality in humans and animals. For example, 8 to 10 million people have been estimated to be infected with the AIDS virus with 263,000 new cases reported in 1990 alone. Many persons infected with the AIDS virus will further suffer from opportunistic infections, such as *Candida albicans*, which causes mucocutaneous fungal disease. Other microbial infections include, for example, *E. coli* diarrhea which is caused by consumption of contaminated food and drinks. This infection affects 40–50% of visitors from industrialized countries travelling to developing countries. Gonorrhea, which is caused by a gram negative bacterium, was reported in over seven hundred and fifteen thousand cases in the United States in 1990, and 3,000 to 10,000 new cases per 100,000 people are diagnosed per year in Africa.

Antibiotic resistant strains of *E. coli* as well as other bacterial, viral, and fungal pathogens, make treatment of many diseases difficult and expensive. Even in cases where a disease may potentially be treated by antibiotics, the unavailability of adequate storage facilities for antibiotics, especially in underdeveloped regions of the world where diseases often are endemic, results in the inability to provide effective treatment to infected populations.

In vertebrates, polymorphonuclear leukocytes, including neutrophils and granulocytes have a central role in combatting infectious disease. These white blood cells contain membrane-bound, cytoplasmic granules, which store various components of their microbicidal arsenal. Upon infection, neutrophils engulf the invading microorganisms in membrane-bound vesicles. These vesicles then fuse with the cytoplasmic granules, exposing the microbes to the toxic contents of the granules. One mechanism granulocytes have for killing such microbes consists of an array of peptides that act as naturally-occurring antibiotics. These peptides, which are generally cationic, mediate their toxicity by interacting with and permeabilizing the cell membranes of various microorganism.

Two families of microbicidal peptides have previously been isolated from granulocytes. The bactenecins, described by Genarro et al., Infect. Immun. 57:3142–46 (1989), Romeo et al., J. Biol. Chem. 263:9573–75 (1988), and Marzari et al, Infect. Immun. 56:2193–97 (1988), are proline and arginine-rich peptides that range in size from 1600 to 8000 daltons which were identified in part by their reactivity with a monoclonal antibody raised against a granule protein extract. The bactenecins are toxic to fungi and gram negative bacteria and, to a lesser extent, to gram positive bacteria.

The defensins are a family of fifteen peptides which constitute 5% to 18% of the cellular protein in neutrophils of various species. This class of molecules has been described by Ganz et al., Eur. J. Haematol. 44:1–8 (1990), Lehrer et al., U.S. Pat. Ser. No. 4,543,252, and Selsted et al., Infect. Immun. 45:150–154 (1984). The defensin peptides consist of 29 to 34 amino acids, with four to ten of these residues being arginine. In addition, they all share six conserved cysteine residues that participate in intramolecular disulfide bonds. Defensins are microbicidal to gram negative and gram positive bacteria, fungi, and certain enveloped viruses.

While the availability of naturally-occurring antibiotic peptides is extremely valuable for treating infectious diseases that are not otherwise amenable to treatment by synthetic antibiotics, the usefulness of bactenecins and defensins suffers from various limitations. For example, both bactenecins and defensins are immunogenic and, therefore, treatment using these compounds could potentially result in anaphylactic or delayed hypersensitivity-type responses. The defensins have also been demonstrated to exhibit substantial in vitro cytotoxicity toward mammalian cells. Furthermore, the requirement for proper disulfide bond formation can reduce the yield of active defensins synthesized since the active molecule contains three intramolecular disulfide bonds.

Thus, there exists a need for an effective microbicidal peptide that can be easily synthesized in an active form and that is effective against a broad spectrum of microorganisms and does not exhibit undesirable side effects. The present invention satisfies these needs and provides related advantages as well.

SUMMARY OF THE INVENTION

The invention provides a broad spectrum antimicrobial compound that includes a tryptophan-rich peptide exhibiting antimicrobial activity. A method of microbicidal inhibition or microbistatic inhibition of microbial growth is also provided. The method includes administering to an environment capable of sustaining microbial growth a microbicidally or microbistatically effective amount of a tryptophan-rich peptide exhibiting antimicrobial activity.

DETAILED DESCRIPTION OF THE INVENTION

Figure 1A:
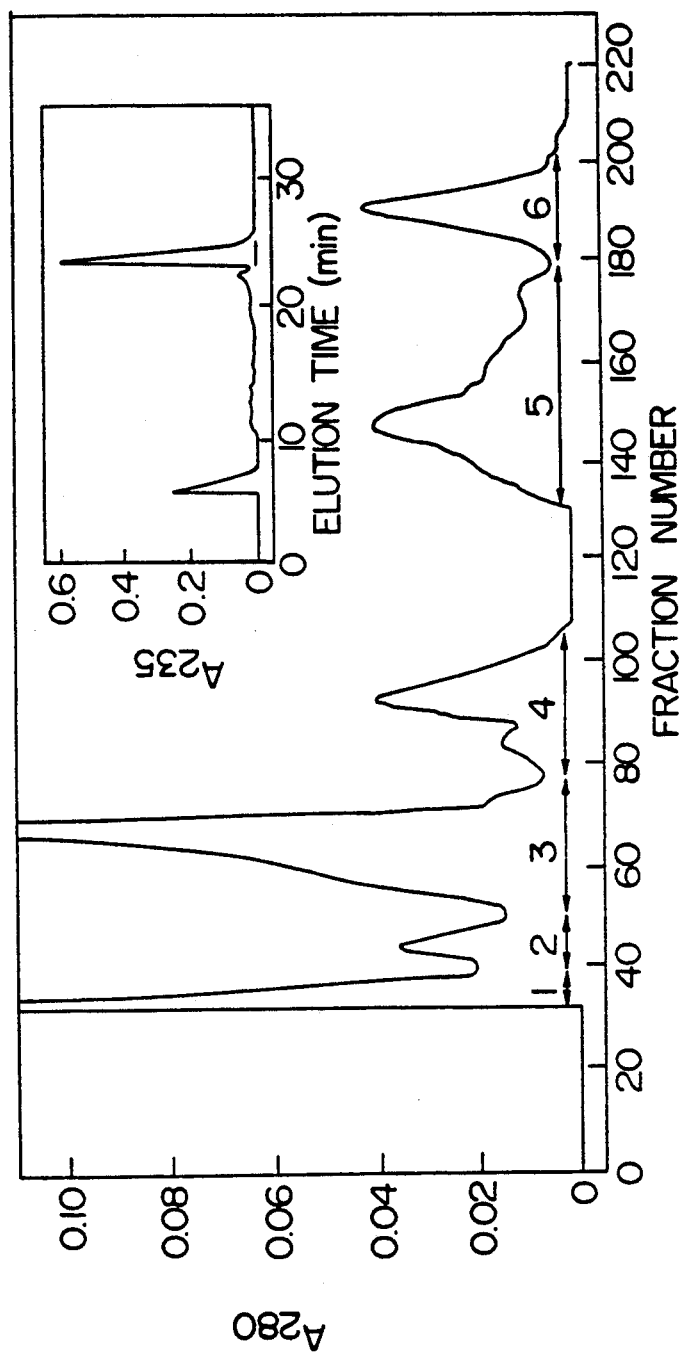
FIG. 1 shows purification of indolicidin. A. Granule extract from bovine neutrophils was chromatographed on Bio Gel P-60 as described in Example II. Peptide from peak 6 was lyophilized and purified by RP-HPLC using a water-acetonitrile gradient containing 0.1% TFA (inset) as described in Example II. The bracket indicates the area of the peak collected. B. Peptide from the RP-HPLC run shown in the inset of FIG. 1A was analyzed in greater detail by a second round of RP-HPLC using water-acetonitrile solvents containing 0.1% TFA, as described in Example II. C. Peptide from the RP-HPLC run shown in FIG. 1A was further analyzed by a second round of RP-HPLC using water-acetonitrile containing 0.13% HFBA, as described in Example II.

The invention is directed to broad spectrum antimicrobial compounds and to methods of their use to inhibit or prevent microbial growth. In one embodiment, the antimicrobial compound of the present invention is a thirteen amino acid peptide purified from bovine neutrophil granules. The peptide is distinguished by its abundance of tryptophan and proline and by the amidation of its carboxy terminus. The indole-rich nature of this peptide together with its microbicidal properties has prompted the name indolicidin for compounds which exhibit these properties. An additional feature of these indolicidins is their low immunogenicity. This property is beneficial for the therapeutic use of indolicidin as an antimicrobial compound since it will not elicit a host immune response.

As used herein, the term "tryptophan-rich" refers to the overrepresentation of a tryptophan amino acid in an antimicrobial compound. The percentage of individual amino acids within a protein varies between each of the twenty naturally occurring amino acids, with tryptophan being the most infrequent. For example, the average occurrence of tryptophan within a protein is about 1 percent whereas the amino acid alanine generally represents about 9 percent of a protein's amino acid content. See, for example, Clapper, M.H., Biochem. Biophys. Res. Comm. 78:1018-1024, (1977). The remaining amino acids exhibit characteristic amino acid frequencies as well. In numerous examples, however, certain amino acids are overrepresented in a protein or protein domain. The abundance of the overrepresented amino acid(s) can vary depending on the size of the protein or domain that is searched. For example, an amino acid residue can be considered abundant within an isolated protein domain without being overrepresented within the entire protein sequence. The abundance of a tryptophan amino acid found within a tryptophan-rich antimicrobial peptide is generally greater than about 20 percent, preferably greater than about 30 percent. A specific example of a tryptophan-rich peptide is the indolicidin peptide shown as SEQ ID NO: 1 whose tryptophan content is about 38 percent.

As used herein, the term "substantially the same sequence" refers to a peptide sequence either identical to, or having considerable homology with, the tryptophan-rich peptide sequence shown as SEQ ID NO: 1. It is understood that limited modifications can be made to the peptide which result in enhanced function. Likewise, it is also understood that limited modifications can be made without destroying the biological function of the peptide and that only a portion of the entire primary structure may be required in order to affect activity. For example, minor modifications of these sequences which do not completely destroy the activity also fall within this definition and within the definition of the compound claimed as such. Modifications can include, for example, additions, deletions or substitutions of amino acid residues, substitutions with compounds that mimic amino acid structure or function as well as the addition of chemical moieties such as amino and acetyl groups. The modifications can be deliberate or can be accidental such as through mutation in hosts which produce tryptophan-rich peptides exhibiting antimicrobial activity. All of these modifications are included as long as the peptide retains its antimicrobial activity.

As used herein, the term "antimicrobial activity" refers to the ability of a compound to inhibit or irreversibly prevent the growth of a microorganism. Such inhibition or prevention can be through a microbicidal action or microbistatic inhibition. Therefore, the term "microbicidal inhibition" as used herein refers to the ability of the antimicrobial compound to kill, or irrevocably damage the target organism. The term "microbistatic inhibition" as used herein refers to the ability of the antimicrobial compound to inhibit the growth of the target organism without death. Microbicidal or microbistatic inhibition can be applied to either an environment either presently exhibiting microbial growth (i.e., therapeutic treatment) or an environment at risk of supporting such growth (i.e., prevention or prophylaxis).

As used herein, the term "environment capable of sustaining microbial growth" refers to a fluid, substance or organism where microbial growth can occur or where microbes can exist. Such environments can be, for example, animal tissue or bodily fluids, water and other liquids, food, food products or food extracts, crops and certain inanimate objects. It is not necessary that the environment promote the growth of the microbe, only that it permit its subsistence.

The invention provides a broad spectrum antimicrobial compound that includes a tryptophan-rich peptide exhibiting antimicrobial activity. The antimicrobial compound includes substantially the same amino acid sequence as the peptide shown as SEQ ID NO: 1. The broad spectrum antimicrobial compound described herein can be purified, for example, from bovine neutrophil granules. Methods for isolating the peptide wherein it is substantially free from other cellular and granule contaminants are described in detail in Example I. Modifications to this procedure that increase the in vivo production of granulocytes and thus the yield of indolicidin peptides can additionally be employed. These modifications can include, for example, administering to the host organism certain growth factors, such as granulocyte-colony stimulating factor (G-CSF), that increase granulocyte proliferation.

Alternatively, the tryptophan-rich antimicrobial peptides can be chemically synthesized using synthesis procedures known to one skilled in the art. Preferably, an automated peptide synthesizer such as Milligen, Model 9050 (Milligen, Milliford, MA) is used in conjunction with $N^\alpha$-Fmoc amino acids on a polyethylene glycol-polystyrene (PEG-PS) graft resin. Suitable linkers such as a peptide amide linker (PAL) can be used, for example, to create carboxamide end groups.

Shown as SEQ ID NO: 1 is the amino acid sequence of a tryptophan-rich peptide that exhibits antimicrobial activity. In contrast to other anti-microbial peptides known in the art, this indolicidin peptide is abundant in tryptophan residues, and to a lesser extent, proline residues. The peptide consists of 13 amino acid residues having an apparent molecular weight of about 2000 daltons. Five of the thirteen residues are the indole-containing tryptophan amino acid whereas three residues of the sequence are prolines. Another distinctive feature of this peptide is the presence of a carboxy terminal arginine amide.

It is known that certain modifications of the primary sequence can be made without completely abolishing activity. Such modifications include the removal of the carboxy terminal amide and the carboxy terminal arginine residue. Additionally, the indole-containing side chains of the tryptophan residues can be oxidized to one or more indole derivatives and the peptides still retain sufficient antimicrobial activity to inhibit the growth of microorganisms. Peptides containing other modifications can additionally be synthesized by one skilled in the art. Such peptides can be tested for retention or enhancement of antimicrobial activity using the teachings described herein. Thus, the potency of indolicidin peptides can be modulated through various changes in the amino acid sequence or structure.

The invention provides a broad spectrum antimicrobial compound exhibiting antimicrobial activity effective against classes of organisms such as gram positive bacteria, gram negative bacteria, fungi and viruses. The unexpected properties of the tryptophan-rich peptide described herein indicate a different mechanism of action and broader spectrum of activity than those of other antimicrobial peptides known in the art. Given the abundance of indole-containing side chains and their propensity to partition into membranes, it is envisioned that the antimicrobial properties of indolicidin peptides are a function of its interaction with target cellular envelopes. The antimicrobial activity of the tryptophan-rich peptide is effective against organisms as diverse as *Staphylococcus aureus, Escherichia Coli, Listeria monocytogenes, Salmonella typhimurium, Candida albicans* and *Cryptococcus neoformans*, for example. The growth of other organisms such as viruses, especially enveloped viruses, can also be inhibited with tryptophan-rich antimicrobial compounds. It is reasonable to expect that other species of these organisms will be similarly susceptible to inhibition with tryptophan-rich antimicrobial compounds.

The invention also provides a method of microbicidal or microbistatic inhibition of microbial growth in an environment capable of sustaining microbial growth. The method includes administering to the environment an effective amount of a tryptophan-rich peptide exhibiting antimicrobial activity.

The tryptophan-rich peptide described herein can be used in a variety of procedures for the treatment or prevention of microbial growth. Such procedures include the microbicidal inhibition of growth where the organisms viability is completely and irreversibly inhibited as well as the microbistatic inhibition of growth where the organisms proliferation is inhibited. Inhibition of growth through either mechanism is effective for the treatment or prevention of microbial growth.

The tryptophan-rich antimicrobial compound can be used, for example, as a therapeutic agent, food preservative or disinfectant. Specific therapeutic uses include, for example, antibacterial, antifungal and antiviral therapeutic agents. The peptide can be administered to a human or animal subject in any of a variety of physiological buffers. Such buffers preferably will contain a low ionic strength solution of neutral pH such as 10 mM sodium phosphate buffer. However, a variety of other buffers can also be used wherein significant microbicidal activity and the majority of the microbistatic activity is retained. Such buffers include, for example, phosphate buffered saline, normal saline and Krebs ringers solution. Moreover, divalent cations such as calcium and magnesium, which are known to inhibit the defensin antimicrobial peptides, do not inhibit the antimicrobial properties of indolicidin peptides. Thus, these cations can be included within the indolicidin preparation if it is beneficial to the therapeutic treatment of a microbial growth. Other compounds or compositions can also be administered in conjunction with indolicidin peptides to further increase their antimicrobial properties. For example, indolicidin peptides can be administered in conjunction with bactenecins, defensins or antibiotics. Compounds such as EDTA, which disrupts microbial membranes, can be included as well.

Peptides can be administered to the subject by, for example, intravenous injection, intraperitoneal injection, orally or in the form of an aerosol spray composition. Lipid vesicles or lipid emulsion preparations containing the peptides can also be used for administering the peptides to a human or animal subject. Specific modes of administration will depend on the pathogen to be targeted. One skilled in the art will know which method is best suited for the particular application.

Food and food products can also be treated with indolicidin peptides for use as a food preservative or to eliminate potential pathogens. For example, shell fish and poultry products routinely harbor the growth of enteric pathogens which can cause severe human disease. Such pathogens can be eliminated by treatment with indolicidin peptides. Food crops such as fruits, vegetables and grains can also be treated with indolicidin peptides to reduce or eliminate post harvest spoilage caused by microorganisms. The peptides can be administered, for example, topically or by transgenic expression of the recombinant peptide. Transgenic expression is known to one skilled in the art and can easily be performed given the nucleic acid encoding the tryptophan-rich peptide described herein (SEQ ID NO: 2).

Additionally, indolicidin peptides can be used as a disinfectant agent to sterilize or maintain microbe-free products. Essentially, any product where microbial growth is undesirable, such as substances which come into contact with animals and humans, can be treated with indolicidin peptides to prevent microbial growth. Such products can include, for example, baby wipes, diapers, bandaids, towelettes, make-up products, eyewash and contact lens solutions. Indolicidin peptides can be administered, for example, topically or in an appropriate buffer.

Effective amounts to be administered for any of the previously described uses will vary depending on the target pathogen and severity of the infection or growth. Higher concentrations are necessary in applications where conditions are somewhat antagonistic of the antimicrobial properties. Typically, between about 0.5 and 500 $\mu$g/ml, preferably between about 1 and 10 $\mu$g/ml, more preferably between about 2 and 5 $\mu$g/ml of peptide is needed to inhibit the growth of about $10^6$ cells/ml of *E. coli*. Indolicidin peptides exhibit similar potencies for other organisms such as *S. aureus, C. albicans, S. typhimurium* and *C. neoformans*. In cases where there are more or less numbers of target organisms the amount of peptide administered can be increased or decreased, respectively. One skilled in the art will know how much peptide should be administered for a desired application given the teachings described herein, or can determine an effective amount following the procedures set forth in Example III.

The following examples are intended to illustrate but not limit the invention.

EXAMPLE I

This example shows the purification of the indolicidin peptide from bovine granulocytes.

Bovine granulocytes ($\geq 97\%$ purity) were purified from fresh blood essentially as described by Carlson and Kanecko, Proc. Soc. Exp. Biol. Med. 142:853–856 (1973), which is incorporated herein by reference. Five hundred ml of citrate anticoagulated bovine blood was centrifuged at $700 \times g$ for forty minutes. The erythrocyte column was collected, made hypotonic by the addition of distilled water, and granulocytes were collected by centrifugation at $120 \times g$ for fifteen minutes. This treatment was repeated twice, until no erythrocytes were detected. The granulocytes were suspended on ice in 20 ml of Hank's balanced salt solution (HBSS). In some experiments, the granulocytes were treated for five minutes with HBSS containing 2 mM diisopropylfluorophosphate (DFP), an inhibitor of serine proteases.

A granule-rich subcellular fraction was obtained by nitrogen cavitation followed by differential centrifugation as described by Borregard et al., J. Cell. Biol. 97:52–61 (1983), which is incorporated herein by reference. The granulocytes in HBSS were pressurized with nitrogen gas for twenty minutes at 750 psi with constant stirring in a nitrogen bomb. Cavitation was performed by release of the pressure over a 2 minute period into an iced vessel. After removal of cell debris by low speed centrifugation, supernatant granules were harvested by sedimentation at $27,000 \times g$ for 20 min at 4 C, and stored at $-80$ C. Granules were typically prepared from one liter of bovine blood containing an average of $4 \times 10^9$ PMN.

Granules collected from 1 to $5 \times 10^{10}$ PMN were extracted with 10 to 50 ml of ice cold 10% acetic acid (pH<3) and stirred for 18 h in melting ice. The suspension was clarified by centrifugation at $27,000 \times g$ and the supernatant was lyophilized. Lyophylate of the acid extract from $1 \times 10^{10}$ cell equivalents was dissolved in twenty ml of 5% acetic acid and fractionated at 4° C. on a $4.8 \times 110$ cm BioGel P-60 (BioRad Laboratories, Richmond, CA) column equilibrated in 5% acetic acid. The column was eluted at 25 ml/h and monitored continuously at 280 nm. FIG. 1 shows the fractionation pattern of proteins eluting from the P-60 column. Indolicidin eluted in the last peak (peak 6), with an elution volume of 5.9 times the void volume. The elution volume of peak 6 exceeded the total volume by nearly 50%, indicating a substantial interaction with the gel matrix.

The peptide in peak 6 was lyophilized and purified by reverse phase high performance liquid chromatography (RP-HPLC) on a $1 \times 25$ cm Vydac C-18 (The Separations Group, Hesperia, CA) column. The column was eluted at 3.0 ml/min using a gradient of water-acetonitrile solvents containing 0.1% trifluoroacetic acid (TFA). The gradient was 0% to 30% acetonitrile in 5 min, then 30% to 45% acetonitrile in 30 min. The inset in FIG. 1 shows that the peptide from peak 6, containing indolicidin, eluted from the HPLC column in a single peak. Approximately 1.5 mg of indolicidin was purified from $1 \times 10^{10}$ cell equivalents of bovine granulocyte granule extract.

EXAMPLE II

This example shows the characterization of the indolicidin peptide preparation obtained from the P-60 column.

Figure 1B:
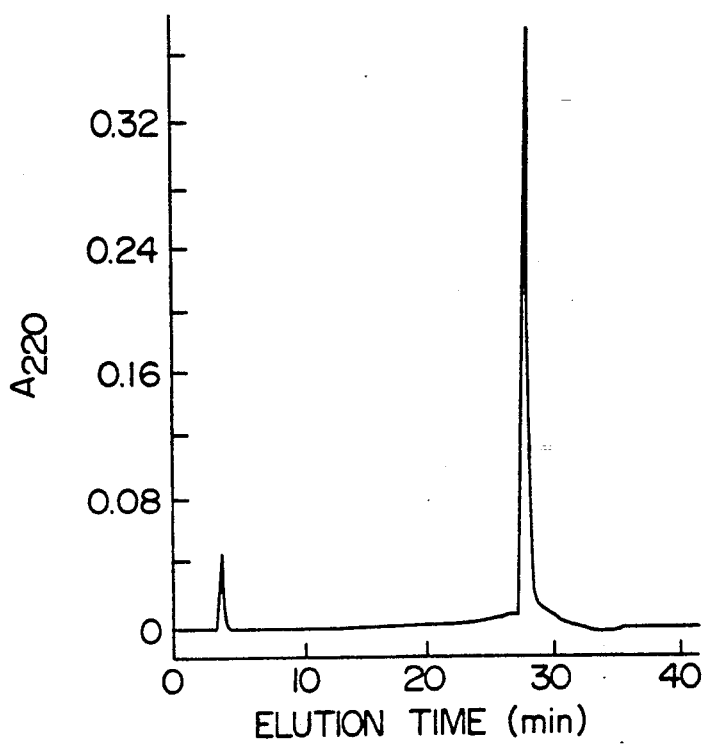
Figure 1C:
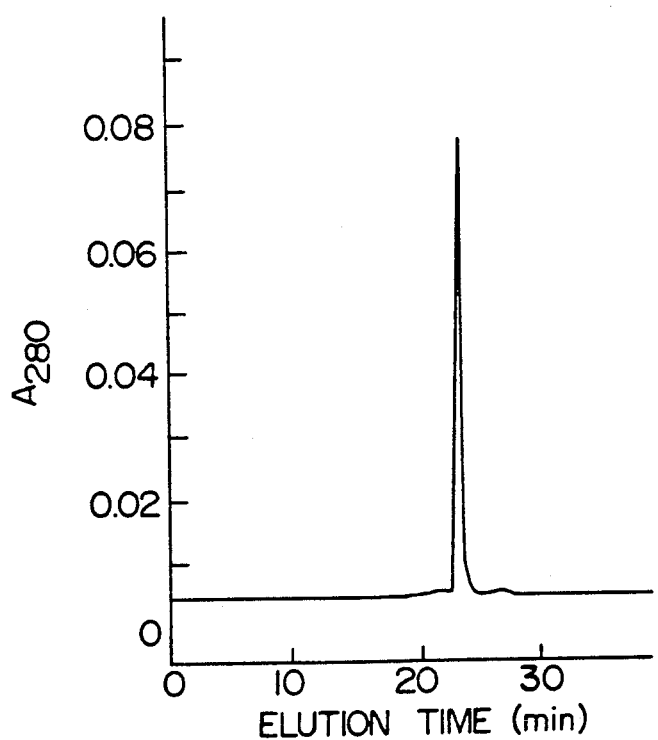

The single peak obtained following RP-HPLC indicated that the indolicidin preparation was relatively pure (FIG. 1A, inset). The homogeneity of the preparation was further examined by a second round of RP-HPLC. In one protocol, the indolicidin fraction from the first RP-HPLC column was analyzed on a $0.4 \times 25$ cm Vydac C-18 column using water-acetonitrile solvents containing 0.1% TFA. Ten micrograms of the indolicidin fraction was chromatographed at 1 ml/min using a 20% to 40% acetonitrile gradient developed over 20 minutes. As shown in FIG. 1B, the indolicidin eluted as a single peak.

In a second protocol, the indolicidin fraction from the first RP-HPLC column was analyzed on a $1 \times 25$ cm Vydac C-18 column using water-acetonitrile solvents containing 0.13% heptafluorobutyric acid (HFBA). Ten micrograms of the indolicidin fraction was chromatographed at 1 ml/min using a 30% to 60% gradient developed over thirty minutes. Again, the indolicidin eluted as a single peak.

Figure 2:
FIG. 2 shows acid-urea PAGE of neutrophil granule extract and purified indolicidin. This 12.5% acrylamide gel was loaded with granule extract from $1.5 \times 10^7$ neutrophils which were either directly lysed (lane 1) or first treated with 2 mM DFP (lane 2); lane 3, 4.3 $\mu$g indolicidin from peak 6 of the P-60 column; lane 4, 2.9 $\mu$g of RP-HPLC purified indolicidin.
Figure 2:
Figure 2:
Figure 2:

The RP-HPLC–purified indolicidin was also examined by polyacrylamide gel electrophoresis (PAGE). The indolicidin appeared as a single band following acid urea-PAGE on a 12.5% acrylamide gel and Coomassie blue staining. (FIG. 2, lane 4). The same banding pattern was observed whether the granules were isolated in the presence or absence of DFP, indicating that indolicidin was not a product of proteolytic degradation occurring during the isolation procedure (FIG. 2, compare lanes 1 and 2). The apparent molecular weight of indolicidin was approximately 2000 daltons, as determined by SDS-PAGE.

Amino acid analysis of the RP-HPLC purified indolicidin was performed by measuring phenylthiocarbamyl derivatives in vapor phase hydrochloric acid (HCl) hydrolysates (24 hours at 110° C.), using the method of Bidlingmeyer et al., J. Chromatogr. 336:93–104 (1984), which is incorporated herein by reference. Briefly, a five microgram sample of indolicidin was hydrolyzed in boiling HCl, then the HCl was removed under vacuum. The hydrolyzed sample was derivatized by the addition of reagent containing ethanol:triethylamine:water:phenylisothiocyanate (7:1:1:1). After incubation at room temperature for twenty minutes, the relative amounts of derivatized amino acids were determined by analytical RP-HPLC. Indolicidin had a minimum composition consisting of two arginine, three proline, one isoleucine, one leucine and one lysine.

Tryptophan was determined spectrophotometrically by analysis of the indolicidin in 6M guanidine hydrochloride, 20 mM sodium phosphate (pH 6.5), as described by Edelhoch, Biochemistry 6:1948–1954 (1967), which is incorporated herein by reference. Indolicidin contained 4.6 tryptophan residues per lysine residue.

The composition of indolicidin was confirmed by automated amino acid sequence analysis using an ABI Model 475A instrument (Applied Biosystems, Inc., Foster City, CA). The peptide sequence contained five tryptophan residues in addition to the eight residues detected in the acid hydrolysate.

The status of the carboxyl terminus was investigated by digestion with carboxypeptidase Y (Pierce Chem. Co., Rockford, IL) and carboxypeptidase B (Boehringer Mannheim Biochemicals, Indianapolis, IN). The presence of a carboxyl terminal arginine amide was first indicated by the lack of release of the carboxyl terminal arginine when indolicidin was incubated for thirty minutes with PMSF-treated carboxypeptidase B. Arginine was released when carboxypeptidase Y was used, presumably due to contaminating trypsin-like endopeptidase and/or amidase activities known to occur frequently in preparation of this enzyme.

The presence of the carboxamide was confirmed by fast atom bombardment mass spectroscopy on a JEOL HX100 HF double focussing magnetic sector mass spectrometer operating at a five kilovolt acceleration potential with a nominal resolution setting of 3000. Lyophilized indolicidin was dissolved in 5% acetic acid and applied to a stainless steel stage. A 6 keV beam of xenon atoms was used to ionize the sample. Spectra were collected and mass assigned in real time using a JEOL DA5000 data system. The observed monoisotopic mass of the protonated molecular ion was 1906.24, which was 0.8 amu less than the 1907.04 calculated for the free acid. In addition, every C-terminal fragment was one mass unit less than that expected for the C-terminal acid. These data indicated that indolicidin was produced by processing events that occurred at both the amino and carboxyl ends of the mature peptide.

The structure determined for the indolicidin peptide was a tridecapeptide amide, shown in the Sequence Listing as SEQ ID NO: 1. This structure confers extremely low immunogenicity properties onto the peptide. In twenty attempts, antibodies have not been generated against this peptide. A sequence similarity search was performed to further analyze the peptide's structure. The search was performed using the non-redundant BLASTP data base. In spite of a number of matches of up to six residues in much larger proteins, the functions of the proteins identified were unrelated or unknown.

EXAMPLE III

This example shows the antimicrobial activity of indolicidin.

Figure 3A:
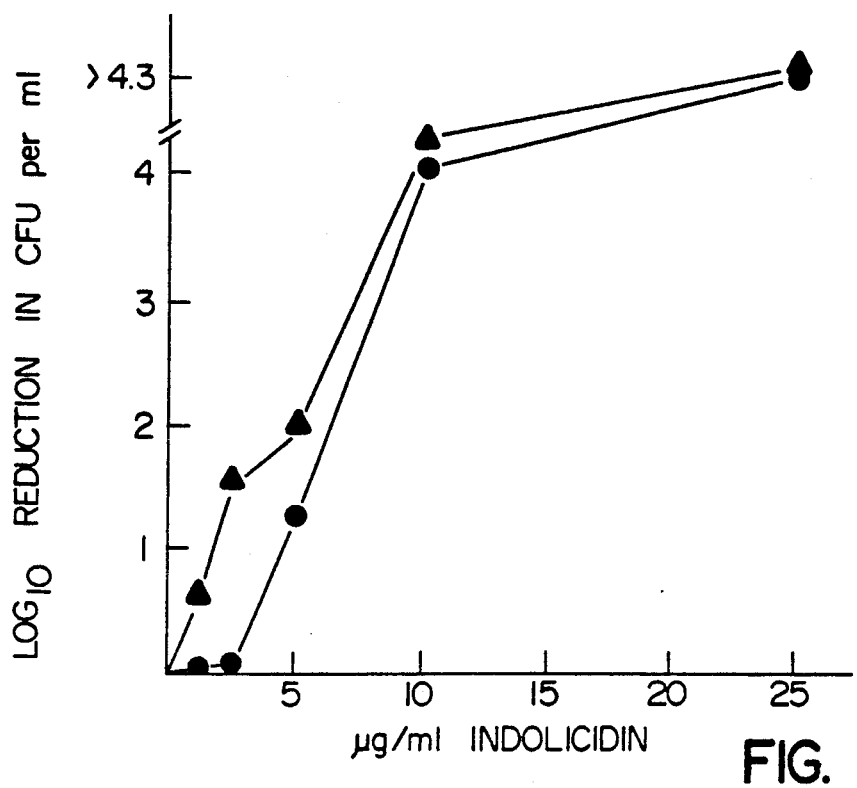
FIG. 3 shows antimicrobial activity of indolicidin A *E. coli* ML-35 (●) or *S. aureus* (△) were incubated with 0 to 25 $\mu$g/ml of indolicidin as described in Example III. Killing is expressed as the $\log_{10}$ reduction in colony forming units (CFU) compared to the control incubation which contained buffer and an appropriate volume of the indolicidin diluent, 0.01% acetic acid. B. Microbicidal kinetics of indolicidin were determined by incubating *E. coli* with 25 μg/ml of indolicidin for intervals up to 40 minutes, as described in Example III.

The time course and dose-dependence of indolicidin antimicrobial activity were determined using a gram negative bacterial strain, *Escherichia coli* ML35, and a gram positive bacterial strain, *Staphylococcus aureus* 502A. Assays were performed in 10 mM sodium phosphate buffer, pH 7.4, at 37° C., as described by Selsted et al., Infect. Immun. 45:150-154 (1985), which is incorporated herein by reference. Both organisms were exceedingly sensitive to indolicidin at low concentrations. $2 \times 10^6$ colony forming units of log phase bacteria were incubated with 0 to 25 ug/ml of indolicidin for two hours, then serially diluted and plated on nutrient agar. Viability was reduced by four logs or more in incubations containing 10 ug/ml of indolicidin (FIG. 3A). *E. coli* was more susceptible than *S. aureus,* as >95% of the input cells were killed in two hours by 2.5 ug/ml indolicidin. The indolicidin diluent, 0.01% acetic acid, had no effect on either bacterial strain.

Figure 3B:
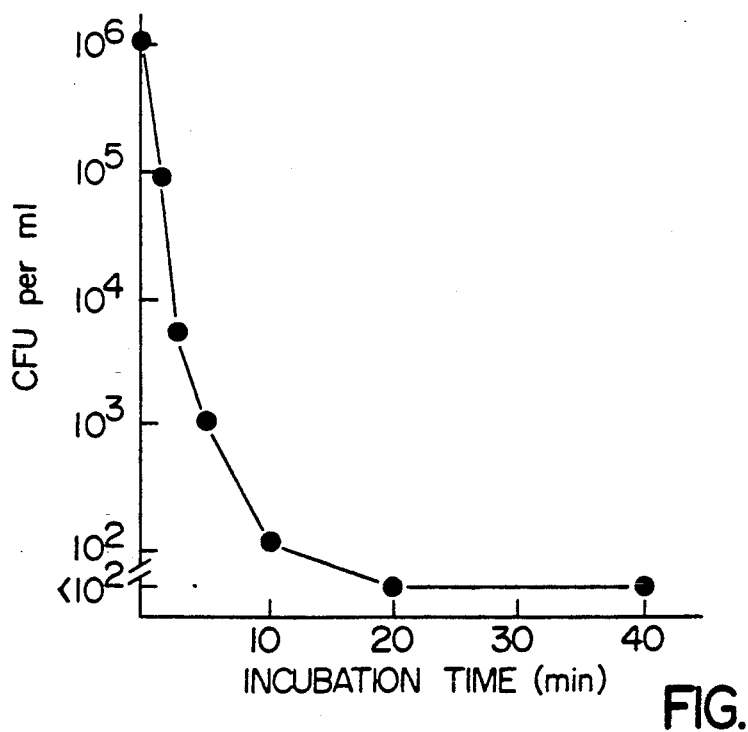

Microbicidal kinetics were evaluated by incubating $2 \times 10^6$ *E. coli* with 25 ug/ml of indolicidin for periods of 1 to 40 minutes. Within five minutes, there was a three log reduction of *E. coli* colony forming units. The culture was virtually sterilized after incubation for twenty minutes in the presence of 25 ug/ml indolicidin (FIG. 3B).

Although the invention has been described with reference to the presently-preferred embodiment, it should be understood that various modifications can be made by those skilled in the art without departing from the invention. Accordingly, the invention is limited only by the claims.

---

---

We claim:

1. An isolated broad spectrum antimicrobial peptide compound having the amino acid sequence of SEQ. ID. NO. 1.

2. The antimicrobial compound of claim 1 further comprising a carboxy terminal amide.

3. The antimicorbial compound of claim 1, wherein said peptide exhibits low immunogenicity.

4. The antimicorbial compound of claim 1, wherein said antimicrobial activity is effective against classes of oranisms selected from the group consisting of gram positive bacteria, gram negative bacteria, fungi and viruses.

5. The antimicrobial compound of claim 4, wherein said organisms are selected from the group consisting of *S. aureus, E. coli, C. albicans, S. typhimurium* and *C. neoformans.*

6. A method of microbicidal inhibition or microbistatic inhibition of microbial growth in an environment capable of sustaining microbial growth comprising administering to said environment a microbicidally or microbistatically effective amount of an antimicrobial compound having the amino acid sequence of SEQ. ID. NO. 1.

7. The method of claim 6, wherein said peptide further comprises a carboxy terminal amide.

8. The method of claim 6, wherein said peptide further exhibits low immunogenicity.

9. The method of claim 6, wherein said antimicrobial activity is effective against classes of organisms selected from the group consisting of gram positive bacteria, gram negative bacteria, fungi and viruses.

10. The method of claim 9, wherein said organisms are selected from the group consisting of *S. aureus, E. coli, C. albicans, S. typhimurium* and *C. neoformans.*

11. The method of claim 6, wherein said environment is a human or animal organism.

12. The method of claim 6, wherein said environment is a food or food product.

13. The method of claim 6, wherein said environment is a water supply.

14. The method of claim 6, wherein said environment is an inanimate substance where microbial growth is undesirable.

15. The method of claim 6, wherein said effective amount is between about 0.5 and 500 μg/ml final concentration.

* * * * *

UNITED STATES PATENT AND TRADEMARK OFFICE
CERTIFICATE OF CORRECTION

PATENT NO. : 5,324,716
DATED : Jun. 28, 1994
INVENTOR(S) : Selsted et al.

It is certified that error appears in the above-indentified patent and that said Letters Patent is hereby corrected as shown below:

In column 5, line 30, please delete "Coli" and insert therefore --coli--.

In column 6, line 36, please delete "SEQ ID NO: 2" and insert therefore --SEQ ID NO: 1--.

In column 7, line 30, please insert --°-- after 4 and before C.

In column 7, line 31, please insert --°-- after -80 and before C.

In column 10, lines 1, 4, 7, 10 and 14, please delete "ug/ml" and insert therefore --µg/ml--.

Signed and Sealed this

Twenty-second Day of November, 1994

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ile  Leu  Pro  Trp  Lys  Trp  Pro  Trp  Trp  Pro  Trp  Arg  Arg
 1                  5                        1 0
```